(12) United States Patent
Muller et al.

(10) Patent No.: US 6,485,488 B1
(45) Date of Patent: Nov. 26, 2002

(54) DEVICE FOR REVASCULARIZING MUSCULAR TISSUES

(75) Inventors: Gerhard Muller, Berlin (DE); Kai Desinger, Berlin (DE); Brita Schaldach, Berlin (DE)

(73) Assignee: Laser-und Medizin-Technologies GmbH Berlin, Berlin (DE)

( * ) Notice: Subject to any disclaimer, the term of this patent is extended or adjusted under 35 U.S.C. 154(b) by 0 days.

(21) Appl. No.: 09/508,885
(22) PCT Filed: Aug. 7, 1998
(86) PCT No.: PCT/DE98/02321
§ 371 (c)(1), (2), (4) Date: May 17, 2000
(87) PCT Pub. No.: WO99/13784
PCT Pub. Date: Mar. 25, 1999

(30) Foreign Application Priority Data

Sep. 17, 1997 (DE) .......... 197 40 825

(51) Int. Cl.[7] ............... A61B 18/12
(52) U.S. Cl. ............... 606/41; 606/32; 606/45; 606/48

(58) Field of Search ............ 606/27–37; 600/41, 600/48, 49, 50, 510; 604/22, 49, 52, 114, 280; 607/102, 101, 122

(56) References Cited

U.S. PATENT DOCUMENTS

| | | | | |
|---|---|---|---|---|
| 5,683,366 A | * | 11/1997 | Eggers et al. | 604/114 |
| 5,873,855 A | * | 2/1999 | Eggers et al. | 604/114 |
| 6,030,380 A | * | 2/2000 | Auth et al. | 606/41 |

FOREIGN PATENT DOCUMENTS

EP 0 808 607 11/1997

* cited by examiner

*Primary Examiner*—Lee Cohen
*Assistant Examiner*—Henry M. Johnson
(74) *Attorney, Agent, or Firm*—Christie, Parker & Hale, LLP

(57) ABSTRACT

A muscular tissue revascularizing apparatus. First electrodes generate a heat effect into the muscular tissue. Second electrodes generate pulsed spark discharge shockwaves into the muscular tissue.

64 Claims, 3 Drawing Sheets

DEVICE FOR REVASCULARIZING MUSCULAR TISSUES

BACKGROUND OF THE INVENTION

The invention concerns a device for revascularizing muscular tissue by producing a tubular necrosis.

Such devices are known and are finding increasing clinical application, in particular in the field of cardiac surgery.

In the category of "transmyocardial laser revascularization", such as laser myocardial revascularization (LMR), predominantly three different laser systems, i.e., pulsed $CO_2$ laser, pulsed holmium-YAG laser, and pulsed excimer laser are currently used, primarily devices from the US companies PLC, CARDIO GENESIS, and United States Surgical Corporation. With these pulsed laser. systems, it is possible, through the use of the mechanism of so-called photoablation, to create transmyocardial channels; and, based on the system, thermally affected marginal zones and also shock waves are produced through the process of photoablation. These systems are extremely expensive, and, even so, amplitude and depth of effect of the shock waves cannot be optimized.

SUMMARY OF THE INVENTION

The object of the invention is, consequently, to provide a comparatively simple and economical device for revascularizing muscular tissue, in particular heart muscular tissues, which offers improved possibilities for optimization of the treatment parameters.

The invention includes the technical teaching of providing a device with which, independently of one another, the wall of a tubular necrosis or of the channel generated in the course of revascularization can be deliberately affected thermally and with which shock wave-like pressure amplitudes with separately adjustable parameters can at the same time be generated in the vicinity of the wall.

It also includes the idea of using different energy sources to produce the thermal effects on the one hand and the shock wave effects on the other, in the interest of separate control of the parameters. According to investigations by the inventor, the combined use of HF energy and electrical pulses with relatively high field intensities of an electrical shock wave generator is particularly economical and presents advantageous effects. The HF energy is expediently in the range of a few watts and the pulse field intensity is a few kV/cm.

Surprisingly, it turned out that the use of bifilar, helically wound high frequency electrodes, which are mounted mutually isolated on an puncture needle, causes shrinkage of this tissue upon input of the high frequency energies and distribution in the parietal tissue. After removal of the puncture needle, an open channel remains. At the same time, by deliberate variation of the high frequency energy, the heat introduced into the channel wall can be deliberately varied with a view to the expansion and consistency of the remaining tissue. Similar effects were also obtained with other HF electrode configurations.

By the additional installation of two mutually isolated high-voltage electrodes, which can lie exposed on the end or along the HF application system (the HF puncture needle), it is also possible to produce a spark-like puncture by the brief application of zero-potential high voltage, which in turn produces shock waves in the vicinity.

By variation of the high voltage in the duration of the high-voltage pulse, it is possible—independently of the introduction of thermally active HF energy via the bipolar HF electrodes—to separately vary the strength of the shock wave amplitudes. Through selection of different bipolar electrode configurations, it is possible to control the thermal coagulation zone.

In a preferred exemplary embodiment, the HF puncture needle is made of a break-resistant ceramic metal composite capillary, on whose outside wall the bipolar HF electrodes are installed and in whose interior the leads of the HP electrodes are guided mutually isolated and attached on the edges of the distal end. However, other suitable materials, such as high temperature resistant plastics (PBEK, PPSU, etc.), may also be used as electrode carriers.

According to a preferred exemplary embodiment, the HF puncture needle is exchangeably mounted in an electrically, mechanically, or hydraulically driven advancing device located in the interior of a hand piece. The hand piece itself is advantageously designed with a distal attachment holder such that during use of the device for perforation of the heart muscle, anchoring in the epicardium is possible and the puncture needle can be inserted under control into the heart muscle by means of the advancing device.

Energy is supplied to the HF electrodes by a bipolar high frequency generator with adjustable output and appropriately adapted terminating impedance; the high-voltage pulse electrodes are supplied by a high-voltage pulse generator.

In further development of the idea according to the invention, to produce larger channel diameters, a rotating hollow knife by which the contour of the channel is cut into the tissue can be provided instead of the puncture needle. The addition of a suction pump on the above-described hand piece makes it possible to aspirate the excess tissue in the interior of the hollow knife.

BRIEF DESCRIPTION OF THE DRAWINGS

Advantageous improvements of the invention are presented in detail within the framework of the description of the preferred embodiments of the invention with reference to the figures which depict.

DETAILED DESCRIPTION OF THE INVENTION

Figure 1:
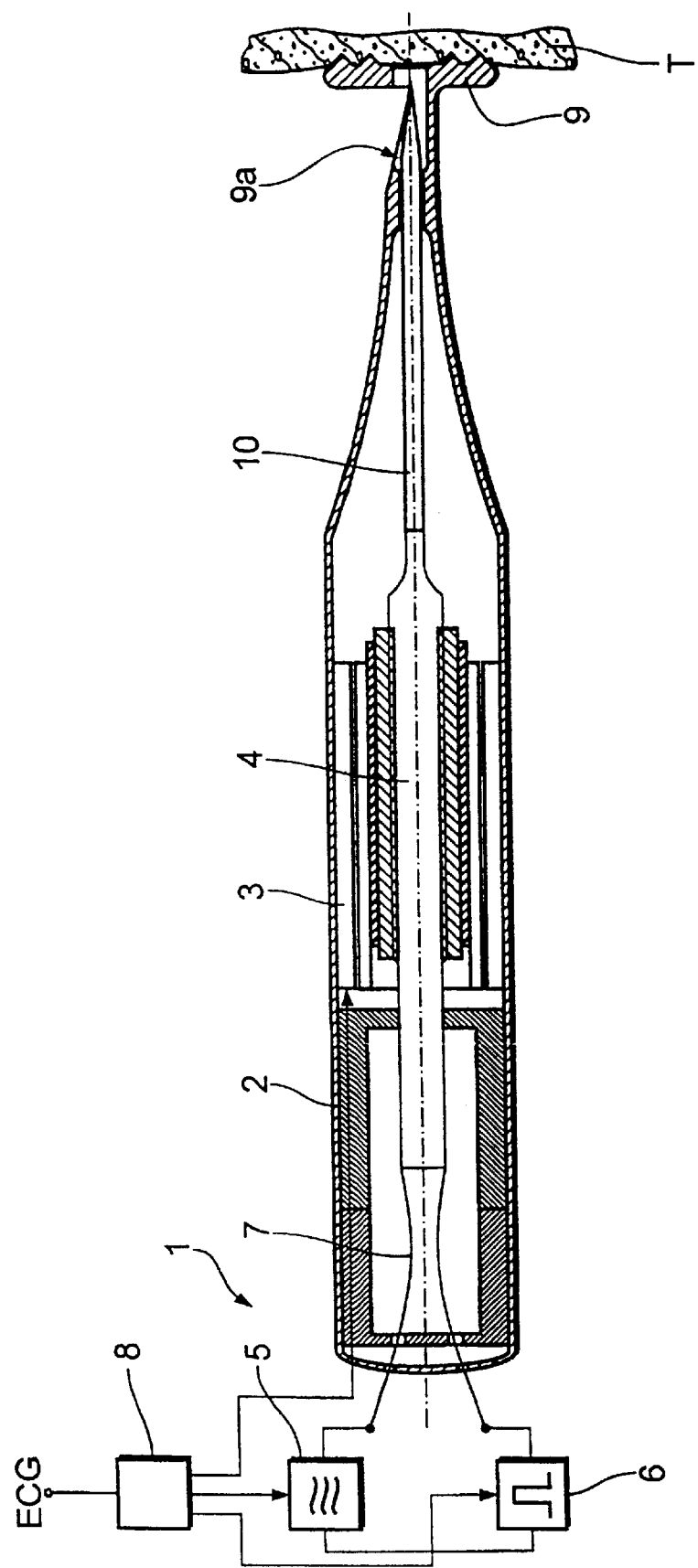
FIG. 1 a device according to one exemplary embodiment of the invention depicted in longitudinal cross-section, FIGS. 2a–2c additional embodiments in side views, FIG. 3 a cross-sectional depiction of the hollow point of the device according to FIG. 1, and FIG. 4 a side view of another embodiment.

FIG. 1 depicts, as an example for a device according to the invention, an application system 1 with an instrument or hand piece 2, an electrical drive unit 3 accommodated therein, and an HF assembly 4, which can be displaced linearly in the axial direction by means of the drive unit 3 against a zone of body tissue T.

Distally coupled to the HF assembly 4 is an applicator, the bipolar puncture needle 10, which can output both the electrical energy generated by a controllable HF generator 5 and that from a controllable high-voltage pulse generator (shock wave generator) 6 to surrounding tissue (not shown). The electrical connection of the HF assembly 4 with the puncture needle 10 to the voltage generators 5, 6 takes place via flexible leads 7. A process control unit 8 is provided to actuate the drive 3 as well as the voltage generators 5, 6 as a function of the EKG signals ECG reflecting heart movements.

Through a laterally open area 9a, a positioning plate 9 provided on the distal end of the hand piece 2 with a tissue holding arrangement enables precise visually supported positioning of the applicator 10 in the operating field.

For a revascularizing treatment of the heart, the hand piece 2 is placed with the positioning plate 9 on a selected epicardial zone and—after preselection of the treatment parameters, such as HF power, pulse amplitude, and pulse repetition frequency as well as advancing speed, etc.—in synchronization with the heart activity by means of the process control 8 and the drive 3, the puncture needle 10 is pushed into the tissue, and simultaneously HF power as well as a voltage pulse is introduced into the tissue and then the puncture needle is again withdrawn.

Figure 2A:
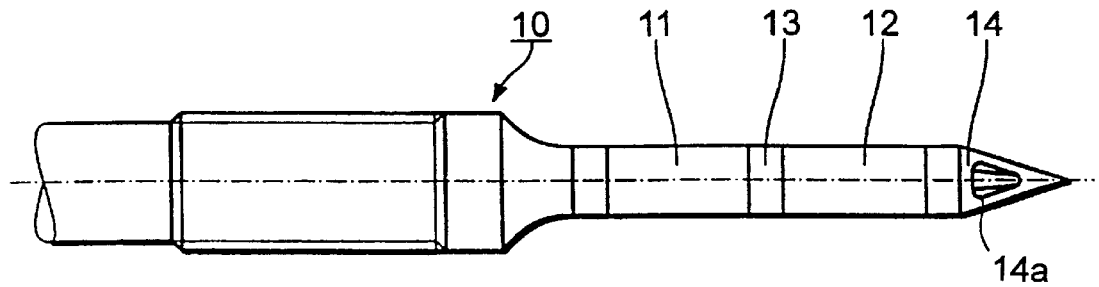
Figure 2B:
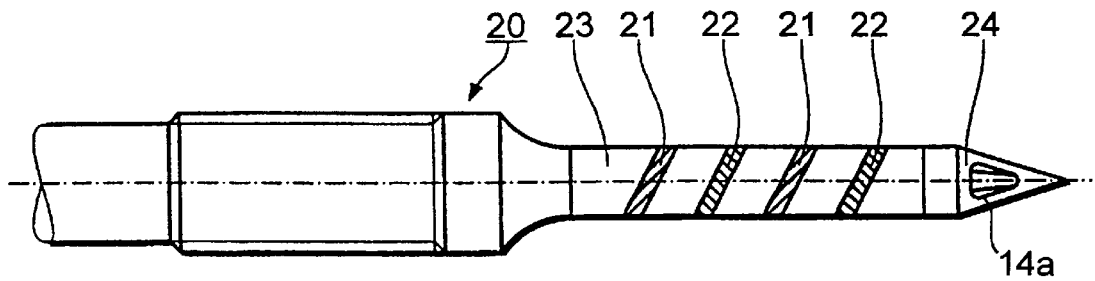
Figure 2C:
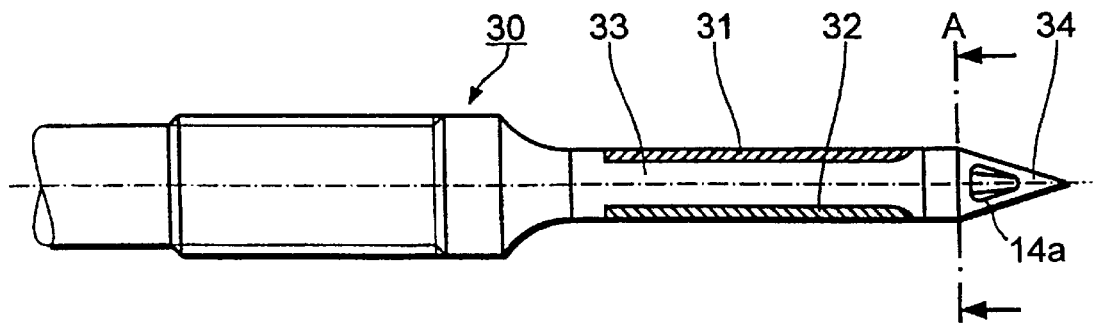

FIG. 2a through 2c depict different embodiments of HF applicators (puncture needles) 10, 20, and 30, respectively, which are used in an overall structure which corresponds fundamentally to the structure depicted in FIG. 1 and described above.

Figure 3:
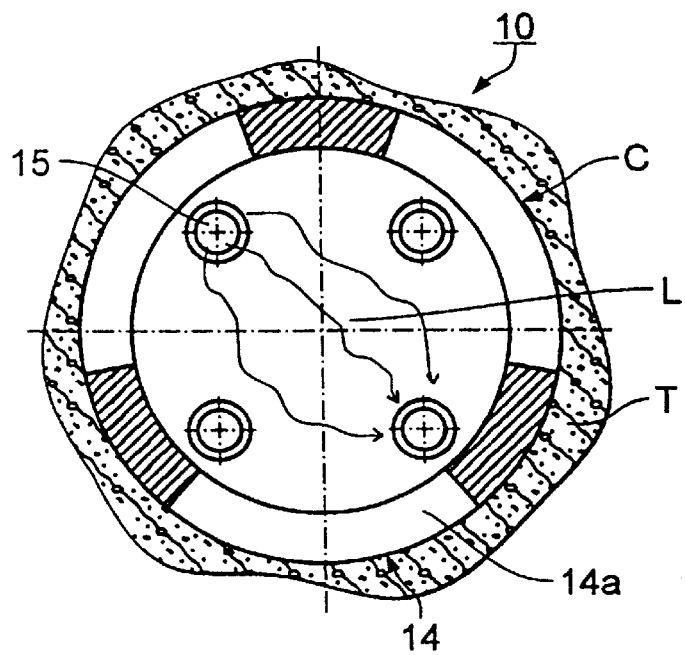

The applicator 10 in FIG. 2a has two electrodes 11, 12 of equal length and equal diameter separated by an isolating zone 13 arranged one behind the other in the direction of the longitudinal axis on the distal end, there is a hollow point 14 with lateral openings 14a Pulse electrodes are arranged inside this point (see FIG. 3).

The applicator 20 according to FIG. 2b has two bifilar electrodes 21, 22 wrapped on the basic body 23, which are at different potential during use. A hollow point 24 on the distal end has the same structure as described above with regard to FIG. 2a.

The applicator 30 in FIG. 2c has two electrodes 31, 33 [sic 32] extending in axial direction arranged in parallel on a dielectric basic body 33. This applicator 30 also has a hollow point 34 on the distal end, as described above.

FIG. 3 depicts a cross-section of the transition zone between the cylindrical section and the hollow point of the HF applicators along the cutting plane A—A.

There, four pulse electrodes 15 are arranged spaced such that a pulsed arc discharge L can develop between them, the energy of which passes through the openings 14a of the point 14 into the surrounding tissue T in which a channel C is formed by means of the applicator and produces a shock wave.

Figure 4:
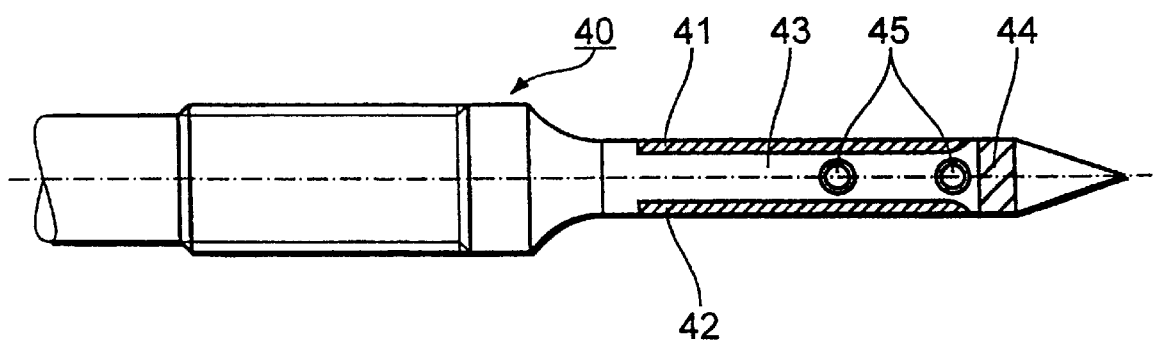

FIG. 4 depicts as another embodiment an applicator 40, wherein the I-IF electrodes 41, 42 are arranged on the carrier body 43 as in the embodiment according to FIG. 2c, where the pulse electrodes 45 are not arranged in a hollow end, but rather are arranged galvanically isolated on the applicator jacket surface in its cylindrical zone. The point 44 is manufactured as a solid from biocompatible plastic.

The invention is not restricted in its embodiment to the above-reported preferred exemplary embodiments. Rather, a number of variants which make use of the solution presented in differently designed embodiments is possible.

Thus, a simplified embodiment has a manual process controller of the puncture needle advancement and the application of the HF and pulse voltage via a pushbutton on the hand piece. Satisfactory results can also be obtained with this embodiment on the quiescent heart.

What is claimed is:

1. A device for revascularizing muscular tissue, comprising:
   means for providing an input of heat to obtain a heat effect in the muscular tissue; and
   means for providing a shockwave effect in the muscular tissue;
   the means for providing a shockwave effect in the muscular tissue being mutually separated from the means for providing an input of heat to obtain the heat effect.

2. The device according to claim 1,
   wherein the means for providing an input of heat to obtain a heat effect includes controllable means for bipolar application of high frequency energy to effect the input of heat; and
   wherein the means for providing a shockwave effect in the muscular tissue includes controllable means for the production and transfer of electrical pulses to provide shockwaves to the muscular tissue.

3. The device according to claim 2, wherein the means for the production and transfer of electrical pulses include an electrical pulse wave generator.

4. The device according to claim 1, further comprising:
   an applicator, having on the surface of which at least two first electrodes connectable with a high frequency source, the applicator also having a hollow point in which are arranged at least two second electrodes connectable with a pulse voltage source.

5. The device according to claim 4, further comprising the at least two first electrodes being connected with a high frequency source and thy at least two second electrodes being connected to a pulse voltage source.

6. The device according to claim 4, further comprising a device coupled to the applicator to change the position of the first electrodes and the second electrodes in tandem.

7. The device according to claim 6, wherein the device to change the position of the first electrodes and the second electrodes includes a drive device for axial displacement along a longitudinal axis of the applicator.

8. The device according to claim 6 wherein the device to change the position of the first electrodes and the second electrodes changes the position of the first electrodes and the second electrodes by an automatic control device, triggered by heart signals.

9. The device according to claim 6, wherein the device changes the position of the first electrodes and the second electrodes under manual control.

10. The device according to claim 1, wherein the heat effect is a thermal marginal necrosis.

11. The device according to claim 1, wherein the muscular tissue is heart muscular tissue.

12. The device according to claim 4, wherein the applicator includes a puncture needle.

13. A muscular tissue revascularizing apparatus comprising:
   an applicator for penetrating muscular tissue;
   first electrodes electrically isolated from each other on the applicator, the first electrodes generating a heat effect into the muscular tissue; and
   second electrodes located within the applicator and spaced to allow a pulsed spark discharge between the second electrodes, the second electrodes generating pulsed spark discharge shockwaves into the muscular tissue.

14. The muscular tissue revascularizing apparatus of claim 13,
   wherein the second electrodes are housed in a hollow portion of the applicator proximate to an applicator tip, the hollow portion having apertures thereon;
   wherein the first electrodes are located on the applicator remote from the applicator tip; and
   wherein the pulsed spark discharge shockwaves are discharged through the apertures into the muscular tissue.

15. The muscular tissue revascularizing apparatus of claim 13, further comprising a high voltage pulse generator coupled to the second electrodes for providing electrical pulse signals.

16. The muscular tissue revascularizing apparatus of claim 15, wherein the high voltage pulse generator applies the electrical pulse signals simultaneous to a high frequency generator applying high frequency electrical signals to said first electrodes.

17. The muscular tissue revascularizing apparatus of claim 13, further comprising a high frequency generator coupled to the first electrodes for providing high frequency electrical signals.

18. The muscular tissue revascularizing apparatus of claim 17, wherein the high frequency generator is a variable high frequency generator for varying high frequency signal energy such that variable heat is injected into the muscular tissue.

19. The muscular tissue revascularizing apparatus of claim 17, wherein the high frequency electrical signals are applied to bipolar first electrodes for injecting heat into the muscular tissue.

20. The muscular tissue revascularizing apparatus of claim 19, wherein the first electrodes are bifilar helically wound electrodes.

21. The muscular tissue revascularizing apparatus of claim 13, wherein the applicator is supported in a housing, and axial displacement of the applicator is controlled by a drive device located within the housing.

22. The muscular tissue revascularizing apparatus of claim 21, wherein the axial displacement of the applicator is controlled in response to heart signals.

23. The muscular tissue revascularizing apparatus of claim 21, wherein the axial displacement of the applicator is controlled manually.

24. The muscular tissue revascularizing apparatus of claim 13, wherein the muscular tissue is heart muscular tissue.

25. The muscular tissue revascularizing apparatus according to claim 13, wherein the heat effect is a thermal marginal necrosis in a channel produced in the muscular tissue.

26. The muscular tissue revascularizing apparatus according to claim 13, wherein the applicator includes a puncture needle.

27. A muscular tissue revascularizing apparatus comprising:
an applicator for penetrating muscular tissue;
first electrodes electrically isolated from each other on the applicator, the first electrodes generating a heat effect into the muscular tissue; and
second electrodes electrically isolated from the first electrodes on the applicator and spaced to allow a pulsed spark discharge between the second electrodes, the second electrodes generating pulsed spark discharge shockwaves into the muscular tissue.

28. The muscular tissue revascularizing apparatus of claim 27, further comprising a high frequency generator coupled to the first electrodes for providing high frequency electrical signals.

29. The muscular tissue revascularizing apparatus of claim 28, wherein the high frequency generator is a variable high frequency generator for varying high frequency signal energy such that variable heat is injected into the muscular tissue.

30. The muscular tissue revascularizing apparatus of claim 28, wherein the high frequency electrical signals are applied to bipolar first electrodes for injecting heat into the muscular tissue.

31. The muscular tissue revascularizing apparatus of claim 27, further comprising a high voltage pulse generator coupled to the second electrodes for providing electrical pulse signals.

32. The muscular tissue revascularizing apparatus of claim 31, wherein the high voltage pulse generator applies the electrical pulse signals simultaneous to a high frequency generator applying high frequency electrical signals to said first electrodes.

33. The muscular tissue revascularizing apparatus of claim 27, wherein the applicator is supported in a housing, and axial displacement of the applicator is controlled by a drive device located within the housing.

34. The muscular tissue revascularizing apparatus of claim 33, wherein the axial displacement of the applicator is controlled in response to heart signals.

35. The muscular tissue revascularizing apparatus of claim 33, wherein the axial displacement of the applicator is controlled manually.

36. The muscular tissue revascularizing apparatus of claim 27, wherein the muscular tissue is heart muscular tissue.

37. The muscular tissue revascularizing apparatus according to claim 27, wherein the heat effect is a thermal marginal necrosis in a channel produced in the muscular tissue.

38. The muscular tissue revascularizing apparatus according to claim 27, wherein the applicator includes a puncture needle.

39. A method for revascularizing muscular tissue comprising:
providing an applicator for penetrating muscular tissue;
locating first electrodes electrically isolated from each other on a surface of the applicator;
locating second electrodes within the applicator, the second electrodes being spaced to allow a pulsed spark discharge between the second electrodes;
pushing the applicator into the muscular tissue;
applying high frequency electrical signals to the first electrodes for generating a heat effect in the muscular tissue; and
applying electrical pulse signals to the second electrodes for generating pulsed spark discharge shockwaves from within the applicator into the muscular tissue.

40. The method of claim 39, further comprising:
housing the second electrodes in a hollow portion of the applicator proximate to an applicator tip, the hollow portion having apertures thereon;
locating the first electrodes on the surface of the applicator remote from the applicator tip; and
discharging the pulsed spark discharge shockwaves through the apertures into the muscular tissue.

41. The method of claim 39, wherein the electrical pulse signals are applied simultaneous to applying the high frequency electrical signals.

42. The method of claim 39, wherein applying high frequency electrical signals further comprises applying the high frequency electrical signals by a high frequency generator.

43. The method of claim 39, wherein applying electrical pulse signals further comprises applying the electrical pulse signals by a high voltage pulse generator.

44. The method of claim 39, wherein applying high frequency electrical signals further comprises applying high frequency electrical signals to bipolar first electrodes to inject heat into the muscular tissue.

45. The method of claim 39, wherein applying high frequency electrical signals comprises varying high frequency signal energy to vary heat injected into the muscular tissue.

46. The method of claim 39, wherein the first electrodes are bifilar helically wound electrodes.

47. The method of claim 39, further comprising supporting the applicator in a housing, and controlling an axial displacement of the applicator by a drive device located within the housing.

48. The method of claim 47, wherein controlling an axial displacement of the applicator is in response to heart signals.

49. The method of claim 47, wherein controlling an axial displacement of the applicator is by manual control.

50. The method of claim 39, wherein the muscular tissue is heart muscular tissue.

51. The method of claim 39, wherein the heat effect is a thermal marginal necrosis in a channel produced in the muscular tissue.

52. The method of claim 39, wherein the applicator includes a puncture needle.

53. A method for revascularizing muscular tissue comprising:

providing an applicator for penetrating muscular tissue;

locating first electrodes electrically isolated from each other on a surface of the applicator;

locating on the surface of the applicator second electrodes electrically isolated from the first electrodes, the second electrodes being spaced to allow a pulsed spark discharge between the second electrodes;

pushing the applicator into the muscular tissue;

applying high frequency electrical signals to the first electrodes for generating a heat effect in the muscular tissue; and applying electrical pulse signals to the second electrodes for generating pulsed spark discharge shockwaves from the applicator into the muscular tissue.

54. The method of claim 53, wherein the electrical pulse signals are applied simultaneous to applying the high frequency electrical signals.

55. The method of claim 53, wherein applying high frequency electrical signals further comprises applying the high frequency electrical signals by a high frequency generator.

56. The method of claim 53, wherein applying electrical pulse signals further comprises applying the electrical pulse signals by a high voltage pulse generator.

57. The method of claim 53, wherein applying high frequency electrical signals further comprises applying high frequency electrical signals to bipolar first electrodes to inject heat into the muscular tissue.

58. The method of claim 53, wherein applying high frequency electrical signals comprises varying high frequency signal energy to vary heat injected into the muscular tissue.

59. The method of claim 53, further comprising supporting the applicator in a housing, and controlling an axial displacement of the applicator by a drive device located within the housing.

60. The method of claim 59, wherein controlling an axial displacement of the applicator is in response to heart signals.

61. The method of claim 59, wherein controlling an axial displacement of the applicator is by manual control.

62. The method of claim 53, wherein the muscular tissue is heart muscular tissue.

63. The method according to claim 53, wherein the heat effect is a thermal marginal necrosis in a channel produced in the muscular tissue.

64. The method according to claim 53, wherein the applicator includes a puncture needle.

* * * * *